United States Patent
Crockatt et al.

(10) Patent No.: US 11,267,796 B2
(45) Date of Patent: Mar. 8, 2022

(54) PRODUCTION OF 2,5-FURANDICARBOXYLIC ACID

(71) Applicant: NEDERLANDSE ORGANISATIE VOOR TOEGEPAST-NATUURWETEN-SCHAPPELIJK ONDERZOEK TNO, 's-Gravenhage (NL)

(72) Inventors: Marc Crockatt, 's-Hertogenbosch (NL); Roel Johannes Martinus Bisselink, Kleve (DE); Roman Latsuzbaia, Delft (NL); Cornelis Petrus Marcus Roelands, Voorschoten (NL); Earl Lawrence Vincent Goetheer, Mol (BE)

(73) Assignee: Nederlandse Organisatie Voor Toegepast-Natuurwetenschappelijk Onderzoek TNO, 's-Gravenhage (NL)

( * ) Notice: Subject to any disclaimer, the term of this patent is extended or adjusted under 35 U.S.C. 154(b) by 111 days.

(21) Appl. No.: 16/487,574

(22) PCT Filed: Feb. 28, 2018

(86) PCT No.: PCT/NL2018/050126
§ 371 (c)(1),
(2) Date: Aug. 21, 2019

(87) PCT Pub. No.: WO2018/160063
PCT Pub. Date: Sep. 7, 2018

(65) Prior Publication Data
US 2020/0055832 A1    Feb. 20, 2020

(30) Foreign Application Priority Data
Feb. 28, 2017 (EP) .................................. 17158488

(51) Int. Cl.
*C07D 307/34* (2006.01)
*C25B 1/02* (2006.01)
(Continued)

(52) U.S. Cl.
CPC .............. *C07D 307/68* (2013.01); *C25B 3/23* (2021.01); *C25B 1/02* (2013.01)

(58) Field of Classification Search
CPC ........... C07D 307/00; C25B 3/23; C25B 3/25; C25B 1/02; C25B 3/05
(Continued)

(56) References Cited

U.S. PATENT DOCUMENTS

2016/0167027 A1* 6/2016 Huang ................. B01J 23/8892
549/485
2017/0197930 A1* 7/2017 Sokolovskii ............... B01J 8/02

FOREIGN PATENT DOCUMENTS

WO    WO 2012/064195 A2    5/2012

OTHER PUBLICATIONS

Chadderdon et al., "Electrocatalytic Oxidation of 5-Hydroxymethylfurfural to 2, 5-Furandicarboxylic Acid on Supported Au and Pd Bimetallic Nanoparticles," Green Chemistry (2014), vol. 16, No. 8, pp. 3778-3786. (Year: 2014).*
(Continued)

*Primary Examiner* — Edna Wong
(74) *Attorney, Agent, or Firm* — BakerHostetler

(57) ABSTRACT

The invention is directed to the to the electrochemical preparation of 2,5-furandicarboxylic acid (FDCA) from 5-hydroxymethylfurfural (HMF) by electrochemical oxidation, comprising a first oxidation step of oxidizing HMF to 5-hydroxymethyl-2-furan-carboxylic acid (HMFCA) in an electrochemical cell, subsequently a first isolation step of isolating HMFCA, followed by a second oxidation step of HMFCA to FDCA.

9 Claims, 3 Drawing Sheets

(51) Int. Cl.
C25B 3/05 (2021.01)
C25B 3/23 (2021.01)
C25B 3/25 (2021.01)
C07D 307/68 (2006.01)

(58) Field of Classification Search
USPC .................. 549/485, 508, 509; 205/427, 637
See application file for complete search history.

(56) References Cited

OTHER PUBLICATIONS

Chadderon et al., "Electrocatalytic oxidation of 5-hydroxymethylfurfural to 2,5-furandicarboxylic acid on supported Au and Pd bimetallic nanoparticles", Green Chemistry, Jan. 1, 2014, 16, 3778-3786.
Grabowski et al., "The electrochemical oxidation of 5-hydroxymethylfurfural with the nickel oxide/hydroxide electrode", Electrochemica Acta, 1991, vol. 36, Issue 13, 1995.
Kim et al., "A review of polymer-nanocomposite electrolyte membranes for fuel cell application", Journal of Industrial and Engineering Chemistry, Jan. 2015, vol. 21, 36-52.
Kwon et al., "Electrocatalytic Hydrogenation of 5-Hydroxymethylfurfural in the Absence and Presence of Glucose", ChemSusChem, Sep. 2013, vol. 6, Issue 9, 1659-1667.
Nilges et al. "Electrochemistry for biofuel generation: production of furans by electrocatalytic hydrogenation of furfurals", Energy & Environmental Science, Aug. 2013, 6, 2925-2931.
Qin et al., "Enzyme-catalyzed selective oxidation of 5-hydroxymethylfurfural (HMF) and separation of HMF and 2,5-diformylfuran using deep eutectic solvents", Green Chemistry, Jan. 1, 2015, vol. 17, No. 7, 3718-3722.
Smitha et al., "Solid polymer electrolyte membranes for fuel cell applications—a review", Journal of Membrane Science, Aug. 2005, 259, 10-26.
Vuyyuru et al., "Oxidation of biomass derived 5-hydroxymethylfurfural using heterogeneous and electrochemical catalysis", Catalysis Today, Nov. 1, 2012, vol. 195, No. 1, 144-154.
Yoo et al., "Polymeric Ionic Liquid and Carbon Black Composite as a Reusable Supporting Electrolyte: Modification of the Electrode Surface", Angewandte Chemie, Mar. 2015, vol. 54, Issue 12, 3744-3747.

* cited by examiner

PRODUCTION OF 2,5-FURANDICARBOXYLIC ACID

CROSS-REFERENCE TO RELATED APPLICATIONS

This application is the National Stage of International Patent Application No. PCT/NL2018/050126, filed Feb. 28, 2018, which claims priority to European Patent Application No. 17158488.1, filed Feb. 28, 2017, the entire disclosures of both of which are incorporated herein by reference for any and all purposes.

The invention is in the field of the preparation of 2,5-furandicarboxylic acid (FDCA). The invention is in particular directed to the preparation of FDCA from 5-hydroxymethylfurfural (HMF).

FDCA is an important compound for the production of biomass-derived polymers such as polyesters, polyamides, polyurethanes and the like. For instance, FDCA can be used as a building block in polyethylene-(PEF) which can be regarded as a bio-based alternative for the petrochemical-based polyethylene terephthalate (PET).

Biomass-derived FDCA is typically prepared in a one-step direct oxidation of HMF. HMF can be obtained from dehydrating carbohydrates (e.g. glucose and fructose) that are found in biomass. One-step direct oxidation of HMF to FDCA can for instance be carried out by thermochemical oxidation, biochemical oxidation or electrochemical oxidation.

The one-step direct electrochemical oxidation of FDCA from HMF by for instance using a Pt/C or a NiO(OH) anode is described in Vuyyuru et al., Catalysis Today 195 (2012), 144-154 and Grabowski et al., Electrochemica Acta 36 (1991), 1995, respectively. In Chadderdon et al., Green Chemistry 16 (2014), 3778-3786, the preparation of FDCA and other oxidation intermediates from HMF in an electrochemical cell using i.a. Pd—Au alloys is described.

WO2012064195 and Qin et al., Green Chemistry 17 (2015), 3718-3722 describe for instance one-step direct biochemical oxidation methods of HMF to FDCA by using genetically modified cells and an enzymatic toolbox respectively. As with other one-step oxidation methods, these one-step biochemical oxidation processes typically provide FDCA together with an undesirable high amount of side products.

Hence, a drawback of one-step direct oxidation methods is the rather unselective oxidation towards FDCA, partially due to the high instability of HMF, resulting in impure and colored FDCA. For the production of polymers from FDCA, FDCA preferably has a purity of least 99.9 mol % and is preferably about colorless (white). FDCA of less than 99.9% purity, generally results in undesirable premature chain termination during the polymerization process and a concomitant poor quality of the polymeric material. Furthermore, brown FDCA generally results in colored materials which are therefore not suitable for some application wherein the color may be importance for commercial reasons in for instance plastics drinks bottles and the like.

Due to the poor solubility of FDCA in standard solvents and due to its high boiling point, FDCA is notoriously difficult to purify by standard techniques such as recrystallization and distillation. Consequently, extensive down-stream-processes are required for the purification of FDCA after its one-step production from HMF.

It is accordingly desired to provide a process for an improved production of FDCA from HMF, which requires less down-stream processing before a suitable purity and color is obtained.

Figure 1:
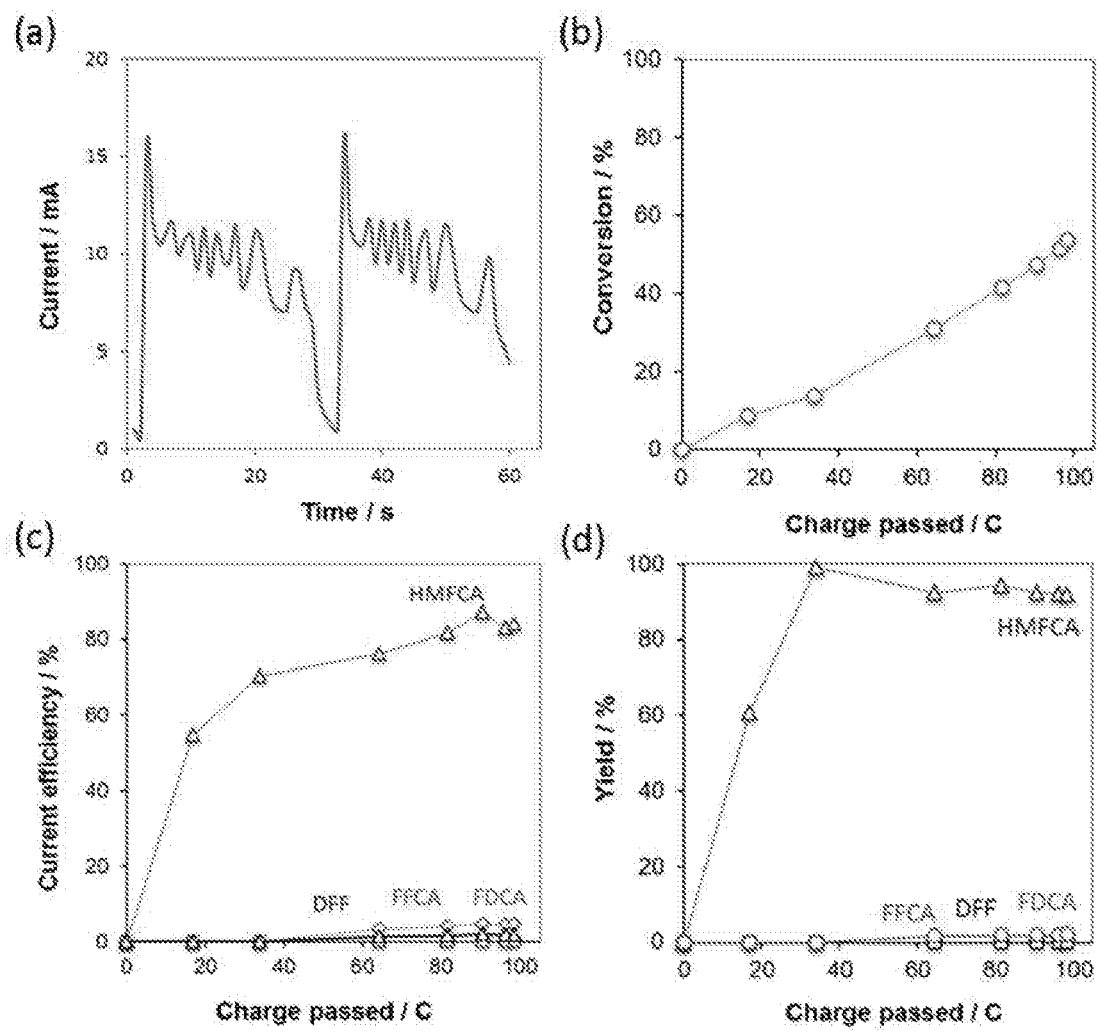
FIGS. 1A-1D are graphs illustrating the oxidation of Example 1.

The present inventors realized that such an improved process can be obtained by using a two-step oxidation process from HMF to FDCA via intermediate 5-hydroxymethyl-2-furan-carboxylic acid (HMFCA) according to the following scheme.

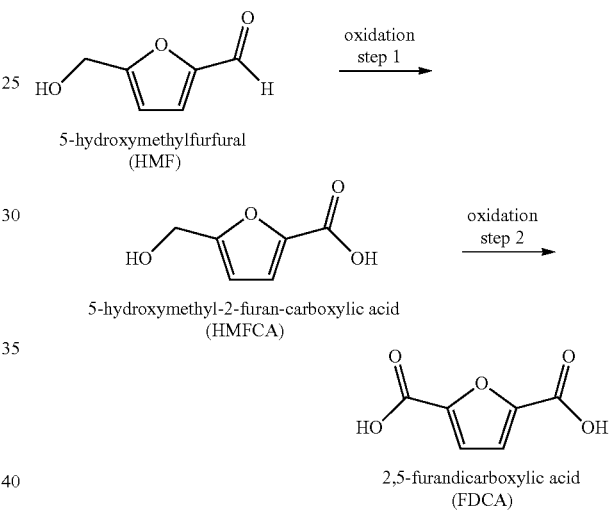

The present inventors found that the intermediate HMFCA is more stable than HMF and can be more easily purified than FDCA. This enables an overall improved process, even though it involves an additional process step vis-à-vis the one-step direct preparation of FDCA from HMF.

The first oxidation step is a direct electrochemical oxidation of HMF to HMFCA and it is carried out in an electrochemical cell. This results in an advantageously selective conversion of HMF to HMFCA.

Accordingly, a first aspect of the invention is a process for electrochemically preparing 5-hydroxymethyl-2-furan-carboxylic acid (HMFCA) from 5-hydroxymethylfurfural (HMF), said process comprising a first oxidation step of oxidizing HMF to HMFCA in an electrochemical cell, and subsequently a first isolation step of isolating HMFCA.

The first oxidation step and isolation of HMFCA is preferably directly followed by a second oxidation step of HMFCA to FDCA. Given the relatively high stability of HMFCA compared to that of HMF, a range of oxidation processes are suitable for this purpose. Examples of suitable oxidation processes for the second oxidation step include commonly used thermochemical, biochemical and electrochemical oxidations.

Although these one-step processes may mechanistically and/or theoretically proceed via intermediates such as HMFCA, one-step processes differ significantly from the present invention ill e.g. that no intermediate isolation of HMFCA is carried out and the reaction conditions for the oxidation of the intermediate can not be set separately from the conditions for the oxidation towards this intermediate. The isolation of HMFCA can be carried out by extraction, solidification such as crystallization, or a combination thereof. HMFCA is considerably better soluble than FDCA in standard solvents, which enables a much easier isolation with solvent-based techniques such as extraction and crystallization.

The first oxidation step of the present invention is carried out in an electrochemical cell comprising an anode and cathode compartments which are typically separated by an ion-exchange membrane. A highly selective oxidation of HMF to HMFCA has been found in case the anode compartment comprises a gold-comprising anode. Examples of gold-comprising anodes include anodes comprising immobilized metallic gold particles on an inert carrier material such as carbon, anodes essentially consisting of metallic gold or alloys thereof. Preferably, the anode comprises flat electrodes or 3D-electrodes such as metal foams or nanoparticles.

The first oxidation step is typically carried out in an ionically conductive electrolyte, preferably comprising an acid, a base or a salt and/or a buffer depending on the desired process pH. Suitable ionically conductive electrolytes e.g. comprise an aqueous electrolyte solution comprising ammonium, sodium, potassium, calcium, magnesium, chloride, perchlorate, hydrogen phosphate or a combination thereof.

Alternatively or additionally to the ionically conductive electrolyte, a solid polymer electrolyte may be used. In such an embodiment, the catalysts may be situated at both sides of the membrane such that no dissolved salts may be required. Suitable solid polymer electrolytes for this invention may be those known in the field of electrolysis of water for the production hydrogen gas in fuel cells, see for instance Kim et al., Journal of Industrial and Engineering Chemistry 21 (2015) 36-52; Smitha et al., Journal of Membrane Science 259 (2005) 10-26; and Yoo et al., Angewandte Chemie, 54 (2015) 3744-3747.

It was found that the first oxidation step proceeds particularly well if the pH of the solution in which the first oxidation step is carried out has a pH of less than 14, preferably less than 13, more preferably about or less than 12. At a pH of less than 12, HMF is particularly stable such that a high yield of HMFCA may be obtained without HMF degradation products. However, the pH should not be too low as this will hamper the electrocatalytic oxidation reaction. Preferably the pH is therefore more than 10, more preferably more than 11. A pH in the range of 11.5-12.5 is accordingly most preferred.

In accordance with the present invention, the oxidation of HMFCA to FDCA can be carried out at a different pH than the oxidation of HMF to HMFCA since no unstable HMF will be present in this reaction because the HMFCA is isolated before. Thus, advantageously, the present invention enables the decoupling of the oxidation conditions for the provision of FDCA and its intermediate HMFCA such that these conditions can be optimized. In fact, the oxidation of HMFCA to FDCA can also be carried out with oxidation methods other that electrochemically, such as for instance using TEMPO-mediated oxidation, a bio-transformation, and/or oxidation with oxygen or air over a catalyst, wherein the catalyst is for example a cobalt-manganese-bromide catalyst.

The concentration of HMF in the solution in which the first oxidation step is carried out, typically ranges from 0.1 to 2 M, e.g. about 1 M. In general, a higher concentration allows higher productivity. However, a high concentration should not be detrimental to the stability of e.g. HMF.

The first oxidation step takes place in the anode compartment of the electrochemical cell as one half reaction of a redox reaction. The electrochemical cell generally further comprises a cathode compartment that is separated from the anode compartment by a membrane, in which cathode compartment a reduction reaction takes place as the other half reaction to complement the first oxidation reaction. The first oxidation reaction may be schematically represented according to the following scheme:

$$HMF + 2OH^- \rightarrow HMFCA + H_2O + 2e^-$$

In a particular embodiment of the present invention, the reduction reaction in the cathode compartment comprises the generation of hydrogen gas, which may schematically be represent according to the following scheme:

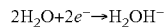

$$2H_2O + 2e^- \rightarrow H_2OH^-$$

In a preferred embodiment of the present invention, the simultaneous reduction reaction in the cathode compartment comprises a reduction reaction of a bio-based compound, such the reduction of HMF or 5-methoxymethylfurfural (also known as 5-MMF) to 2,5-dimethylfuran, or the reduction of furfural to furfuryl alcohol and/or 2-methylfuran.

It may also be possible to carry out the reduction reaction of a carboxylic acid to a alcohol as a simultaneous reduction reaction in the cathode compartment. For instance, the reduction of linear saturated dicarboxylic acids such butanecloic acid, which can also be based on biomass, may provide linear saturated diols such as 1,4-butanediol. Other linear saturated dicarboxylic acids that can be reduced in the cathode compartment to their corresponding diols include ethanedioic acid, propanedioic acid, pentanedioic acid, hexanedioic acid, heptanedioic acid and the like. The reduction reaction of linear saturated dicarboxylic acids can be schematically represented according to the following scheme:

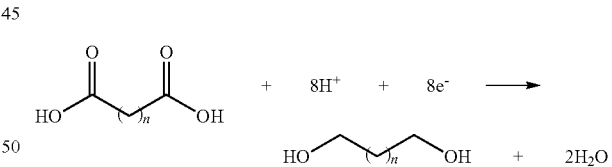

wherein n is zero or a positive integer, preferably 0-8, more preferably 2-6.

Other reduction reaction that can be carried out in the cathode compartment may comprise the reduction HMF to the more stable version 2,5-dihydroxymethylfuran (DHMF), HMF to 2,5-dimethylfuran (DMF) or furfural to 2-methylfuran. Thus, the production of an industrially relevant compound on the cathode allows utilization of otherwise spent on $H_2$ electrons, i.e. energy.

For instance, HMF can be reduced to DHMF on Fe—, Ni—, Ag—, Zn—, Cd— and/or In-comprising electrodes in 0.1 M $Na_2SO_4$ (see e.g. Kwon, Y. et al. ChemSusChem 2013 (6) 1659). HMF can be also reduced to DMF with high efficiencies on Cu-electrode in electrolyte mixture 1:1 of 0.5 M $H_2SO_4$ and ethanol or acetonitrile (Nilges, P. et al. Energy & Env. Sci. 2013 (6) 2925). Furfural may be reduced to 2-methylfuran on Cu- or Pb-comprising electrodes in 0.5 M $H_2SO_4$.

In another particular embodiment of the present invention, the reduction reaction in the cathode compartment comprises oxidation of HMF to FDCA through a mediator. For instance, in this particular embodiment, oxygen is reduced to hydrogen peroxide (i.e. an example of said mediator) on electrodes (e.g. active carbon electrodes) in an alkaline electrolyte (typically at a pH of about 10-12) containing HMF. The peroxide radicals formed in the cathode compartment, are strong oxidizers which can oxidize HMF to FDCA. The oxidation of HMF to FDCA through peroxide could also involve a mediator, such as an N-oxide mediator, such as (2,2,6,6-tetramethylpiperidin-1-yl)oxyl (TEMPO), which can be oxidized by superoxide ($O_2^-$) (which may be produced during $O_2$ reduction) to its oxidized version, which on its turn can oxidize HMF to FDCA.

By reducing a bio-based compound in the cathode compartment, the overall process efficiency and generated value may be increased. In addition, in case a diol is the product of the reduction reaction, this diol can be used in the preparation of polyesters from FDCA.

The first oxidation reaction proceeds particularly well by applying a dynamic potential on the anode. As is known in the art, the potential of an electrode is typically expressed as a potential of said anode versus a reference electrode (RE), for instance a standard hydrogen electrode (SHE) or a saturated calomel electrode (SCE). For the first oxidation reaction of the present invention, typical experimental conditions comprise application of a pulsed potential technique to the gold electrode. For instance, a first pulse typically comprising a potential of 1 V vs SCE may be applied to oxidize or passivate species on the electrode and improve reaction kinetics. Subsequently, a second pulse of typically a potential of about 0.15 V SCE for about 30 s may be used for the oxidation reaction itself. The oxidation may typically be performed in an ionically conductive electrolyte, e.g. 0.1-1 M $Na_2SO_4$ and NaOH (pH 10-12), or 0.1-0.5 M $NaClO_4$ and 0.1-0.5 M phosphate buffer.

The process of the present invention is preferably performed in an H-cell type electrolyzer divided with an anion exchange membrane to avoid reduction of oxidation products on the cathode, or avoid mixing of the anodic and cathodic electrolytes and products. The electrolyte is preferably vigorously mixed to reduce diffusion limitations of the process.

The present invention may be illustrated by the following examples.

EXAMPLE 1

Electrochemical Oxidation of HMF to HMFCA

The electrochemical oxidation of HMF to HMFCA was performed in H-shaped 2-compartment electrochemical cell consisting of two compartments, for anolyte and catholyte, separated with an anion exchange membrane. The anolyte comprised 0.01 M HMF dissolved in 100 ml aqueous buffer of 0.1 M $Na_2HPO_4$ (pH 12) and 0.1 M $NaClO_4$, whereas catholyte consisted of 100 ml aqueous 0.1 M $NaClO_4$. Both electrolytes were vortexed during the conversion and purged with nitrogen. A gold wire (~12 $cm^2$) was used as anode or working electrode (WE) for the oxidation reaction, HMF to HMFCA, platinum gauze was used as a cathode or counter electrode (CE) for the reduction reaction, water reduction to hydrogen and hydroxide-ion.

Prior to the experiments both of the electrodes are washed with a hot water, rinsed with ethanol, acetone and finally demi-water. SCE electrode was used as a reference electrode to control potential at the working electrode. All there electrodes were connected to a potentiostat for the control of the potential at the working electrode. For the conversion reaction following oxidation pulsed potential method was applied, where first pulse of 1 V vs SCE for duration of 1 s is applied to clean the surface of the anode, and second following pulse of 0.15 V vs SCE for duration of 30 s for the oxidation of HMF. These pulses were applied continuously for 14 hours. After the conversion the anolyte content is measured with HPLC and it is taken for the HMFCA extraction. Good conversions and high purities of HMFCA were obtained, as illustrated in FIGS. 1A-1D. For instance, an isolated yield of HMFCA of more than 92 mol % based on the starting amount of HMF having a purity of 95 wt. % or more can be obtained. A decomposition of less than 5 wt % HMF was observed.

COMPARATIVE EXAMPLE 1

Direct Oxidation to of HMF to FDCA

Figure 2:
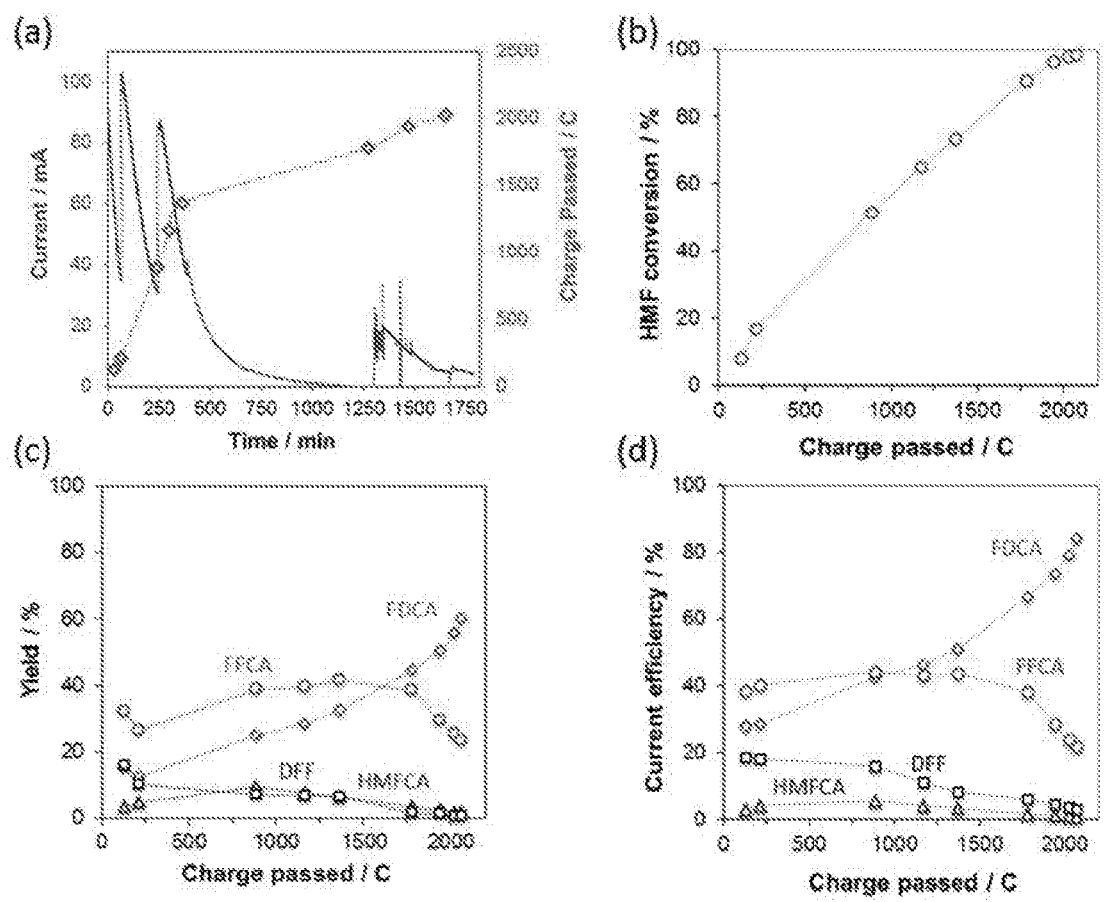
FIGS. 2A-2D are graphs illustrating the oxidation of Comparative Example 1.

The electrochemical oxidation of HMF to FDCA was performed in a similar setup a described in Example 1, with the difference that Ni/NiOOH was used as an anode or the WE and that the anolyte comprised 0.005 M HMF dissolved in the aqueous buffer. The reaction was carried out up to 24 h. Although good a conversion of HMF was obtained, a complex mixture of reaction products was observed as illustrated in FIGS. 2A-2D. The mixture included about FDCA (in a yield of about 60 mol %) together with 2-formyl-5-furancarboxylic acid (FFCA), 2,5-diformylfuran (DFF) and HMFCA. A decomposition of HMF in the range of about 10 to 15 wt % was observed, which is higher than that in Example 1.

EXAMPLE 2

TEMPO-Mediated Oxidation of HMF to FDCA in Cathode Compartment

The TEMPO-mediated oxidation of HMF to FDCA was performed in H-shaped 2-compartment electrochemical cell consisting of two compartments, for anolyte and catholyte, separated with an anion exchange membrane. The catholyte comprised 0.01 M TEMPO, 0.01 M HMF dissolved in 100 ml aqueous buffer of 0.5 M boric acid (pH 9) and 0.3 M $NaClO_4$, whereas anolyte can comprise 100 nil aqueous 0.1 M $NaClO_4$. Both electrolytes were vortexed during the conversion and purged with nitrogen. A gold wire (~12 $cm^2$) was used as the anode or working electrode (WE) for the oxidation reaction. Pt wire was used as a cathode or counter electrode (CE).

Figure 3:
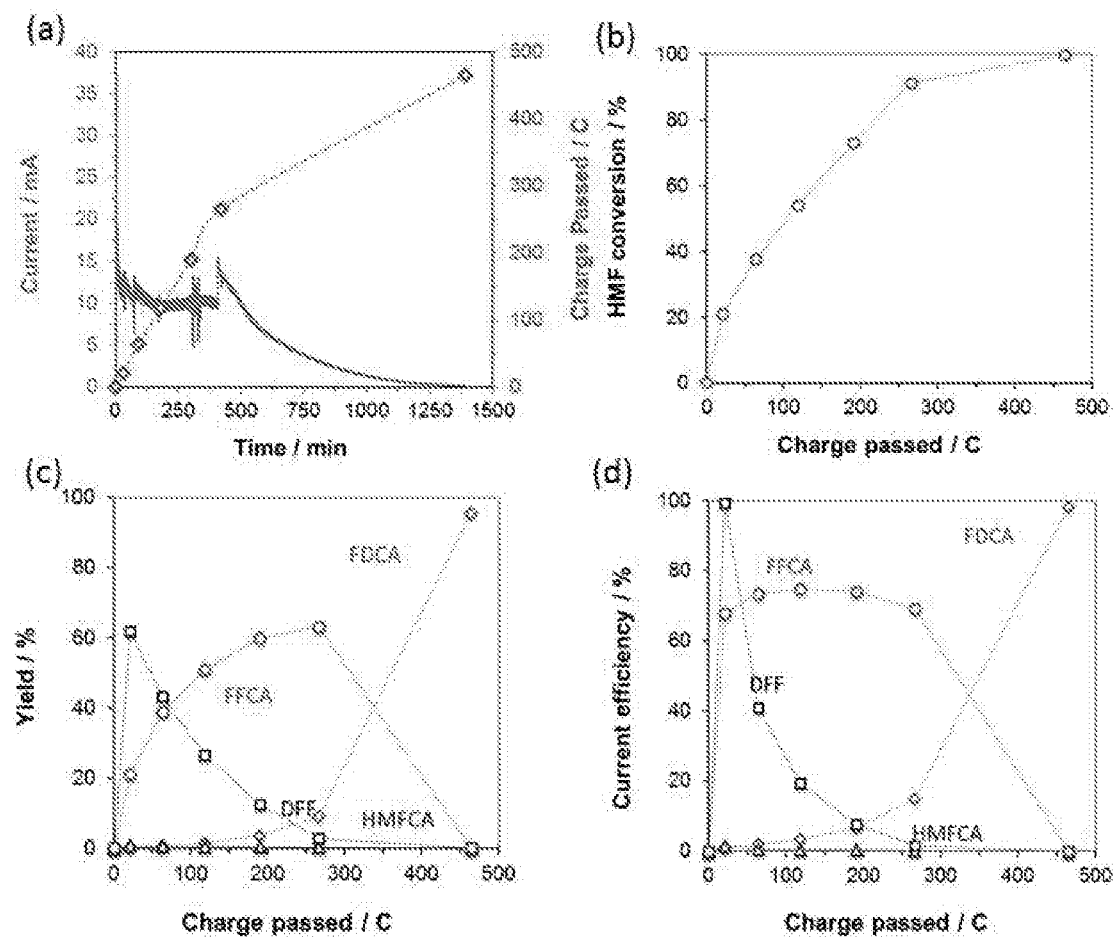
FIGS. 3A-3D are graphs illustrating the oxidation of Example 2.

Prior to the experiments both of the electrodes are washed with a hot water, rinsed with ethanol, acetone and finally demi-water. SCE electrode was used as a reference electrode to control potential at the working electrode. All of the electrodes were connected to a potentiostat for the control of the potential at the working electrode. For the oxidation of TEMPO, a potential of 0.75 V vs SCE was applied. The conversion of the catholyte content is measured with HPLC and FDCA was isolated. Good conversions and high purities of FDCA were obtained, as illustrated in FIGS. 3A-3D. For instance, an isolated yield of FDCA of about 99 mol % based on the starting amount of HMF having a purity of 95 wt. % or more can be obtained. A decomposition of less than 2 wt % HMF was observed.

EXAMPLE 3

TEMPO-Mediated Oxidation of HMFCA to FDCA

The TEMPO-mediated oxidation of HMFCA to FDCA can be carried out similarly as described in Example 2. That is, anode compartment of an H-shaped 2-compartment electrochemical cell consisting of two compartments, for anolyte and catholyte, separated with an anion exchange membrane can be charged with 0.01 M TEMPO, 0.01 M HMFCA dissolved in 100 ml aqueous buffer of 0.5 M boric acid (pH 9) and 0.3 M $NaClO_4$, whereas the catholyte can comprise 100 nil aqueous 0.1 M $NaClO_4$. Both electrolytes were vortexed during the conversion and purged with nitrogen. A gold wire (~12 $cm^2$) was used as the cathode or working electrode (WE) for the oxidation reaction. A clean reaction to FDCA can be observed, in accordance with Example 2, with even less decomposition since HMF is not present. Thus overall, the two-step process shows less HMF decomposition and less production of other undesired side-products.

The invention claimed is:
1. A process for preparing 2,5-furandicarboxylic acid, said process comprising:
   a first oxidation step of oxidizing 5-hydroxymethylfurfural to 5-hydroxymethyl-2-furan-carboxylic acid in an electrochemical cell, wherein the first oxidation step is a direct electrochemical oxidation;
   a first isolation step of isolating the 5-hydroxymethyl-2-furan-carboxylic acid; and
   a second oxidation step of oxidizing the isolated 5-hydroxymethyl-2-furan-carboxylic acid to 2,5-furandicarboxylic acid.

2. The process of claim 1, wherein the oxidation is carried out in a cathode compartment of the electrochemical cell using a mediator.

3. The process of claim 2, wherein the mediator is hydrogen peroxide or an N-oxide mediator.

4. The process of claim 1, wherein the oxidation of the 5-hydroxymethylfurfural to the 5-hydroxymethyl-2-furan-carboxylic acid is carried out in an anode compartment of the electrochemical cell, said anode compartment comprising a gold-comprising anode.

5. The process of claim 1, wherein the electrochemical cell comprises an anode compartment and said anode compartment comprises an electrolyte comprising ammonium, sodium, potassium, calcium, magnesium, perchlorate, sulfate, hydrogen phosphate, a solid polymer electrolyte or a combination thereof.

6. The process of claim 1, wherein the oxidizing of the 5-hydroxymethylfurfural to the 5-hydroxymethyl-2-furan-carboxylic acid is carried out in a solution having a pH of less than 14.

7. The process of claim 1, wherein a reduction reaction of a bio-based compound is carried out in a cathode compartment of the electrochemical cell.

8. The process of claim 7, wherein the bio-based compound is selected from the group consisting of ethanedioic acid, propanedioic acid, butanedioic acid, pentanedioic acid, hexanedioic acid, heptanedioic acid and combinations thereof.

9. The process of claim 1, wherein a reduction is carried out in a cathode compartment of the electrochemical cell, said reduction reaction comprising generating hydrogen gas.

* * * * *